United States Patent
Tufail et al.

(10) Patent No.: US 12,277,707 B2
(45) Date of Patent: Apr. 15, 2025

(54) METHOD, SYSTEM AND FOR GENERATING TREATMENT RECOMMENDATIONS BASED ON IMAGES OF A FACIAL REGION OF A HUMAN SUBJECT

(71) Applicant: VISIONAI GMBH, Ebikon (CH)

(72) Inventors: Adnan Tufail, London Southwark (GB); Yuntai Aaron Lee, Mercer Island, WA (US); Peter Maloca, Lucerne (CH)

(73) Assignee: VISIONAI GMBH (CH)

( * ) Notice: Subject to any disclaimer, the term of this patent is extended or adjusted under 35 U.S.C. 154(b) by 371 days.

(21) Appl. No.: 17/626,002

(22) PCT Filed: Jul. 10, 2020

(86) PCT No.: PCT/EP2020/069619
§ 371 (c)(1),
(2) Date: Jan. 10, 2022

(87) PCT Pub. No.: WO2021/009066
PCT Pub. Date: Jan. 21, 2021

(65) Prior Publication Data
US 2023/0351595 A1    Nov. 2, 2023

(30) Foreign Application Priority Data

Jul. 12, 2019   (CH) ........................... 910/19

(51) Int. Cl.
*G06T 7/00*    (2017.01)
*G16H 20/17*   (2018.01)
*G16H 50/20*   (2018.01)

(52) U.S. Cl.
CPC ........... *G06T 7/0014* (2013.01); *G16H 20/17* (2018.01); *G16H 50/20* (2018.01);
(Continued)

(58) Field of Classification Search
CPC ......... G06T 7/0014; G06T 2207/20081; G06T 2207/30088; G06T 2207/30201;
(Continued)

(56) References Cited

U.S. PATENT DOCUMENTS

2009/0245603 A1*  10/2009  Koruga ................. A61B 5/444
                                                    382/128
2013/0322711 A1*  12/2013  Schultz ................ G06V 10/987
                                                    382/128
(Continued)

FOREIGN PATENT DOCUMENTS

WO    WO 2018/069768 A2    4/2018

OTHER PUBLICATIONS

International Search Report from International Application No. PCT/EP2020/069619, mailed on Sep. 18, 2020.
(Continued)

*Primary Examiner* — Ming Y Hon
(74) *Attorney, Agent, or Firm* — Davidson Kappel LLC

(57) ABSTRACT

A method for generating treatment recommendations based on images of a facial region of a human subject comprises the steps of acquiring at least one image of the facial region and generating image data representing the at least one image; processing the image data and additional information, including at least an indication of a condition affecting an appearance of the facial region and a treatment type to treat the condition, to obtain a treatment recommendation and outputting the obtained treatment recommendation. The processing step includes a comparison substep to compare information derived from the image data with reference information to obtain a reference measure. The processing step further includes a classifying substep to obtain the treatment recommendation (63.1 ... 8, 64.1 ... 8) based on the reference measure.

21 Claims, 4 Drawing Sheets

(52) U.S. Cl.
CPC .............. *G06T 2207/20081* (2013.01); *G06T 2207/30088* (2013.01); *G06T 2207/30201* (2013.01)

(58) Field of Classification Search
CPC ........ G16H 20/17; G16H 50/20; G16H 30/40; G16H 50/70
See application file for complete search history.

(56) References Cited

U.S. PATENT DOCUMENTS

| | | | |
|---|---|---|---|
| 2017/0157962 A1* | 6/2017 | Rabe | B41J 29/023 |
| 2017/0246473 A1 | 8/2017 | Marinkovich et al. | |
| 2017/0330264 A1 | 11/2017 | Youssef et al. | |
| 2020/0038824 A1* | 2/2020 | Charraud | B01F 35/2209 |
| 2020/0046460 A1* | 2/2020 | Jang | A61B 34/10 |
| 2021/0007599 A1* | 1/2021 | Grondin | A61B 3/032 |
| 2021/0027897 A1* | 1/2021 | Rasochova | A61B 5/0077 |
| 2021/0228276 A1* | 7/2021 | Giraldez | G09B 1/00 |

OTHER PUBLICATIONS

Written Opinion from International Application No. PCT/EP2020/069619, mailed on Sep. 18, 2020.

* cited by examiner

METHOD, SYSTEM AND FOR GENERATING TREATMENT RECOMMENDATIONS BASED ON IMAGES OF A FACIAL REGION OF A HUMAN SUBJECT

This application is a U.S. national phase application under 35 U.S.C. of § 371 of International Application No. PCT/EP2020/069619, filed Jul. 10, 2020, which claims priority to a Switzerland Patent Application No. CH 00910/19, filed Jul. 12, 2019, the disclosures of which are all hereby incorporated by reference herein.

TECHNICAL FIELD

The invention relates to a method for generating treatment recommendations based on images of a facial region of a human subject. The invention further relates to a system for generating treatment recommendations based on images of a facial region of a human subject and to a computer program product for that purpose.

BACKGROUND ART

A large number of conditions affect inter alia the appearance of the facial region of a human subject, i. e. a region including the face (i. e. forehead, eyes, nose, cheeks, mouth and chin) as well as parts of the scalp (including the ears) and the neck. Certain features are an indication pointing to a certain condition or the (present) severity thereof (such as twitched facial muscles on one side of the face in the case of hemifacial spasm or a yellowish or greenish colour of the skin or the whites of the eyes in the case of jaundice), other features constitute the condition itself (such as severe wrinkles due to aging tissue). Depending on the condition, certain ways of treatment are available, wherein "treatment" includes medical and cosmetic treatments in particular. If treatment leads to improvement, this will again affect said features. Similarly, based on visual information a relapse of such a condition will most likely be detectable based on visual information of the facial region.

As an example for a cosmetic treatment affecting the visual appearance of the facial region, the use of botulinum neurotoxins (BoNTs) to improve the appearance of facial wrinkles, or to treat medical disorders affecting areas of the human face or in the neighbourhood of the human face has become common.

Human subjects utilise BoNTs in cosmetic procedures because they have noticed signs of ageing. In particular, the cosmetic application of BoNT injections leads to the reduction of facial wrinkles, especially in the uppermost third of the human face. Usually, the application of BoNTs is repeated in regular or irregular intervals as the effect of an injection disappears after a few months. The timing of retreatment depends on a number of factors including but not exclusively, type, dose and location of BoNTs used, previous response to treatment, patient and physician preference, previous side effects, previous dosing and location.

Other means for addressing the effects of facial ageing include gel filler applications, using in particular hyaluronic acid based substances.

Critical to effective treatment with BoNTs or gel fillers is the ability to use these substances to their best effect; this requires, at minimum, an understanding of the scientific profile and physical characteristics of commercially available agents, but just as important are an understanding of the patient-specific factors that will determine the treatment plan and the ability to integrate consideration of each patient's individual needs into the development of a personalized treatment strategy. In the case of BoNTs, ff given too frequently or at excessive dose paralysis may occur that may be cosmetically or medically problematic. In rare cases, vessel-occlusions may occur that lead to consecutive vision impairment or loss. Not treating frequently enough or with suboptimal dosing or position may result in recurrence of symptoms.

Similar principles apply to other conditions that require monitoring at close intervals.

Optimum treatment requires frequent face-to-face examinations of the treated subjects. These examinations are cumbersome for the latter because they need to see their attending professional, which involves travelling and thus necessitates a considerable time (even more if there are waiting times). Accordingly, the number of examinations is usually less than would be optimal for a best-possible treatment. Due to this and the complexities involved in devising a treatment plan, often the outcome of the treatment is not optimal.

SUMMARY OF THE INVENTION

It is the object of the invention to create a method and a device pertaining to the technical field initially mentioned, that allows for an improvement of the treatment of conditions that affect the appearance of a facial region of a human subject.

The solution of the invention is specified by the features of claim 1. According to the invention, the method comprises the steps of
 a) acquiring at least one image of the facial region and generating image data representing the at least one image;
 b) processing the image data and additional information, including at least an indication of a condition affecting an appearance of the facial region and a treatment type to treat the condition, to obtain a treatment recommendation;
 c) outputting the obtained treatment recommendation;
 wherein the processing step includes a comparison substep to compare information derived from the image data with reference information to obtain a reference measure, and
 wherein the processing step further includes a classifying substep to obtain the treatment recommendation based on the reference measure.

A corresponding system for generating treatment recommendations based on images of a facial region of a human subject, comprises
 a) a camera for acquiring at least one image of the facial region and generating image data representing the at least one image;
 b) a processor for processing the image data and additional information, including at least an indication of a condition affecting an appearance of the facial region and a treatment type to treat the condition, to obtain a treatment recommendation;
 c) an interface for outputting the obtained treatment recommendation;
 wherein the processor includes a comparison module to compare information derived from the image data with reference information to obtain a reference measure, and wherein the processor further includes a classifying module to obtain the treatment recommendation based on the reference measure.

The at least one image is acquired by suitable means, in particular by a digital camera, which may be a standalone device or integrated into another device (such as a desktop or notebook computer, webcam, smartphone, tablet computer, digital mirror, etc.). A digital camera generates digital image data representing the image. This image data may be processed in further steps of the method.

The step of processing the image data may include known image processing steps to improve the image quality (e. g. for reducing noise, sharpening the image, correcting imaging errors, etc.), to identify and/or measuring certain structures (e. g. facial structures, wrinkles, spots, etc.) and/or to generate statistical data (e. g. on the colour distribution).

The additional information includes an indication of the condition affecting the appearance of the facial region. This allows for a condition-specific analysis of the image data and for providing condition-specific treatment recommendations. It is possible to provide a number of conditions in order to analyze the same image data specifically for all the indicated conditions.

In addition, the additional information includes a treatment type to treat the condition, such as "local injections of a specified agent", "external application of a specified ointment", "internal use of a certain pharmaceutical substance" or combinations thereof. Again, it is possible to provide a number of treatment types in order to provide recommendations including more than one treatment type if suitable.

Further additional information, provided by the human subject and/or the attending professional and/or obtained from databases may be processed to obtain the treatment recommendation. In particular, this further additional information may include data with respect to previous treatments (used agents, dosage, treatment plans, treatment response etc.). The additional information may affect the processing in the comparison substep, in the classifying substep and/or in a further processing substep prior to outputting the treatment recommendation. Instead or in addition, the additional information may be used for preprocessing the image data.

Outputting the obtained treatment recommendation may include displaying the information on a display (e. g. on a screen) to the human subject and/or his or her attending professional (such as a doctor, another healthcare professional or a cosmetic professional), forwarding the information to a further computer, storing the information in a storage, etc.

Ultimately, the treatment recommendation may be displayed in several ways. Preferably, the recommendation is displayed in the form of a graphical chart to support the patient and attending professionals in optimising retreatment intervals, dose and position of treatment if applicable.

In the comparison substep the image data and/or information derived therefrom is compared with reference information. The reference information has significance with respect to the condition and/or its treatment. It may include in particular earlier images or derived data of the same subject, reference data obtained from other individual subjects or groups of subjects, scores based on a certain well-defined analysis method, etc. The reference information may be obtained from a storage within the system running the method (e. g. earlier image or derived data of the same subject), from a system-specific or publicly available database (such as pooled reference data relating to other individuals), from the human subject and/or his or her attending professional.

The reference measure is the result of the comparison. It may be a binary or ternary information (yes/no, smaller/equal/larger, etc.), a value ("76% agreement") or a multi-dimensional quantity (reference measure vector or matrix). Generally, the reference measure is an assessment of the (local) severity of the condition or its effects on the appearance compared to a standard, a target state or a comparison individual or group and/or of the progression or regression compared to an earlier point in time.

The classifying substep is based on the reference measure and yields the treatment recommendation. In this substep, the examined case is assigned to one or several classes based on the reference measure. An example of a set of possible classes is "treatment", "no treatment", "delayed treatment", "suggested face-to-face examination". Another example of such a set is "treatment with substance A, dosage 1/d", "treatment with substance A, dosage 2/d", "treatment with substance B, dosage 1/d", etc. The treatment recommendation is the totality of assigned classes (such as "delayed treatment", "treatment with substance A, dosage 1/d") or information derived from this totality of assigned classes.

The inventive method and system allow for systematically and automatically analyzing image data which is relevant for a condition affecting the appearance of the facial region of the human subject. It allows for systematically taking into account information relating to conditions or treatments of further subjects and/or relating to the progression or regression history of the condition with the human subject.

It is to be noted that in general the treatment recommendation acts as a decision support only and does neither replace the expertise of the attending professional nor the taking of decisions by the human subject or the attending professional (e. g. with respect to the type of treatment or the treatment plan).

Usually, the inventive method will be executed by a computer program product comprising program code to execute all steps of the inventive method when run on a computer system. The computer program product may be stored on a non-transitory computer readable medium or provided by an electric or optical signal.

The computer system used to run the program and/or to execute the inventive method may include several computing devices and network connections, e. g. a first client located with the human subject, a second client located with the attending professional and a server system located with a service provider, all linked together by (secured) internet connections.

In a preferred embodiment, the comparison substep and the classifying substep include the application of a machine learning algorithm, accordingly, the processor of the inventive system preferably comprises a machine learning module including the comparison module and the classifying module as submodules. The application of the machine learning algorithm implicitly involves the comparison of the derived information with reference information (obtained from learning data) as well as classifying a reference measure obtained from the comparison (classification, regression, clustering, etc.). Both steps may be integrated into a single process, i. e. the two submodules are in fact a combined machine learning module. Several machine learning algorithms may be used in the context of the invention, including Support Vector Machines, artificial neural networks, deep learning, cluster analysis, etc. In particular, the learning data includes or consists of pooled (anonymized) data of other users of a system providing a service based on the inventive method. This means that the service is constantly improved and updated.

Preferably, the image is acquired by a computing device of the human subject, the image data is transmitted from the mobile computing device to a server and the processing step is carried out by the server based on the received image data.

Accordingly, in the inventive system, the camera is comprised by a computing device of the human subject, the computing device further comprising the acquisition module and a first transmitter module to transmit image data, and the processor is comprised by a server including a second transmitter module for receiving the image data from the computing device. The image data may be uploaded to a storage assigned to the server or to a cloud storage, the server has access to.

Preferably, the computing device of the human subject is a general-purpose device such as a desktop computer, most preferably a mobile device such as a notebook computer, a smartphone, a tablet computer, or a digital mirror. This ensures that the computing device is usually available to most users, and the human subject is familiar with the operation of the specific device. Mobile devices allow for acquiring images even when the human subject is travelling. Both supports the regular and frequent acquisition of images by the human subject and thus the close monitoring of the effects of a certain condition. The number or frequency of face-to-face examinations of the human subject may be lowered without compromising the success expectations of the treatment. In fact, it will be possible to increase the number of examinations, if necessary, without substantially burdening the human subject and without substantial costs.

In a preferred embodiment, a message will notify both the patient and the attending professional at a likely optimum time to retreat, including information on specific parameters of the suggested treatment.

The inventive method and system ensure that images of the relevant facial region are reproducibly acquired and processed.

Preferably, the acquiring step includes acquiring a plurality of images of the facial region. Accordingly, the camera of the inventive system is operated to acquire a plurality of images and to forward the image data representing the plurality of images to the processor. This allows for improving the image data and/or data derived from the image data. First of all, taking a plurality of pictures improves the statistics, which is helpful in case of imaging errors, movements of the human subject introducing in-motion unsharpness, borderline illumination etc. Furthermore, a plurality of images may represent different parts of the facial region and/or the facial region in different illumination (e. g. light from above, below, right, left, frontal), from different viewing angles and/or with different facial expressions (smiling, frown, raised eyebrows, opened and closed eyes, etc.). This allows for obtaining much more information with respect to the appearance of the facial region. The information on the different views (e. g. with respect to illumination, viewing angle or facial expression) may be provided for the processing of the image data (especially if the human subject is instructed to change any of the parameters mentioned) or it may be derived automatically from the image data itself.

The number of images to be taken may depend on the condition. As an example, if the condition affects several parts of the facial region and if high resolution pictures of all these parts are needed the number of images to be taken will be bigger than in the case of a condition locally affecting the facial region or conditions where an overview image of the facial region is sufficient to assess the degree of the condition or the effects of treatment.

Preferably, the acquiring step includes acquiring video images of the facial region. Accordingly, the camera of the inventive system has the capability of obtaining video images. Video images relate to a plurality of images that represent a certain temporal sequence of images, e. g. taken in predetermined short time intervals (lying e. g. in the range of 1 ms to 1 s). Video images are easily taken by usual camera devices and allow for the fast generation of image data covering different viewing angles, facial expressions or parts of the facial region.

In alternative embodiments, the acquiring step consists of acquiring a single still image of the facial region. The image may be accepted if it fulfills certain requirements or discarded if imaging errors or other shortcomings are detected. In this case, a further image will be acquired.

In a preferred embodiment, the reference information comprises image data obtained from an image of the facial region of the human subject taken at an earlier point in time. Accordingly, the inventive system comprises storage means or interface means providing access to storage means, wherein the image data is stored. This allows for the assessment of the tendencies of the development of the condition and/or of the result of a therapy or treatment. The difference in time between the image data relating to the reference information and the present image data corresponds in particular to typical treatment time scales (such as days, weeks or months depending on the condition and the treatment). Preferably, both the image data for the reference information as well as the present image data are obtained by the same method and under the same circumstances. Alternatively, reference information images may be obtained from an external source. They may show the facial region of the human subject at a younger age (childhood, young adulthood, prior to the emergence of the condition, etc.). Furthermore, in principle, earlier image data may be used if it does not cover all the facial region of interest but just overlaps in some subregions.

Alternatively, instead of earlier image data, or in addition, other reference information, e. g. relating to average healthy subjects or to average subjects suffering the condition, is employed.

Preferably, the treatment recommendation includes at least one of the following:
- a treatment substance recommendation (relating e. g. to a certain active ingredient, a specific pharmaceutical or a subtype of therapy);
- a dosage recommendation;
- a treatment location recommendation (especially for injections or external applications of a substance, pointing to a certain part or certain parts of the facial region);
- a treatment timing recommendation (this may include an advice with respect to taking further images, depending on the condition and previous response);
- an examination recommendation (e.g. including an advice to see an attending professional or the recommended time of the next face-to-face examination).

The recommendation may include more than one of the above mentioned items. It may amount to a comprehensive treatment regimen or treatment plan and include a combination of more than one kind of treatment.

Alternatively, the recommendation is just binary information of whether a certain predetermined treatment should be applied or not or whether the subject should see an attending professional or not.

Advantageously, the acquiring step includes a substep of providing instructions to the human subject affecting the at least one acquired image of the facial region. Accordingly, the inventive system preferably comprises an acquisition module for guiding the human subject to acquire the at least one image.

The instructions may be provided through different channels, e. g. by an auditory and/or visual indication. The instructions relate in particular to the extent of the facial region covered by the image (and/or the corresponding zoom factor), the viewing angle, the direction and intensity of illumination, and/or the facial expression. It may be checked based on the image data whether the human subject followed the instructions. It is also possible to perform a real-time check of the image information provided by the camera, e. g. based on image recognition techniques, and providing feedback to the user (establishing a feedback-loop) and/or trigger the taking of an image only if the respective conditions are fulfilled. The triggering may happen automatically, such that the human subject does not have to worry about to manually operate the release at the right point in time. This ensures that optimum images of the right facial area are obtained, in a standardised and repeatable way.

In a particularly preferred embodiment, where the camera is comprised by a computing device of the human subject, the application software running on this computing device guides the human subject with respect to the acquisition of the images, and preferably, the real-time image information from the camera is analyzed by the computing device in order to update the guidance information provided to the subject.

As mentioned, in a preferred embodiment, the substep of providing instructions includes an instruction to the human subject to assume a certain facial expression. Accordingly, the acquisition module is operated to present a corresponding instruction to the human subject. Facial expressions affect the position of some of the facial muscles. The instructions may be in text form, such as "raise eyebrows as high as possible", "grin", "frown", "close left eye", etc. or they may be in visual form, e. g. in the form of cartoon-style or pictogram style illustrations or photos of people showing the desired expression.

Often, it is not critical that the human subject assumes a certain "standardized" facial expression, but it is more relevant that the expression is about the same in different examination sessions and that the expression allows for a better assessment of the effects of the condition affecting the appearance.

In certain preferred embodiments, the condition is an aesthetic condition and the treatment type is a cosmetic treatment. A number of treatment types fall into the category of "cosmetic treatment", in particular the external application of a substance (e. g. in the form of cremes or ointments), the local injection of a substance or the intake of a composition.

In a particular embodiment, the cosmetic treatment comprises an application of botulinum neurotoxin injections in the facial region. This allows for the reduction of facial wrinkles, especially in the uppermost third of the human face, especially wrinkles due to ageing.

In a further embodiment, the cosmetic treatment comprises an application of gel filler injections in the facial region. Such applications of dermal fillers, using e. g. hyaluronic acid based substances, allow for the correction of soft tissue defects of the face, in particular due to facial aging.

In the case of a BoNT and/or gel filler treatment, the human subject and the attending professional may be supported by the inventive method or system to optimize the treatment and to improve the results. The recommendation preferably includes an indication on the optimum locations of treatment. The indication may be supplemented by a dosage information for the identified locations. In addition, the recommendation may include information with respect to an optimum treatment interval and direct the human subject to see the attending professional, if needed.

Images may be captured immediately before treatment and in suggested time intervals after the treatment. Treatment data may be provided to the processor, such that the information on specific effects of a certain treatment detected in a certain cycle of the treatment may be used in all further cycles.

The invention is not restricted to the application in connection with BoNT or gel filler injections. It may be applied in connection with the treatment of further conditions affecting the appearance of the facial region (including the appearance of the eye or ocular region), such as:
  myasthenia gravis,
  endocrine orbitopathy (associated effects like lid lag as Graefe's sign etc.),
  systemic steroid side effects affecting the appearance of the face,
  lid paralysis and its recovery,
  orbital/lid tumor,
  blepharitis,
  hordeolum,
  chalazion,
  allergic diseases,
  acne, etc.

Applications include the treatment of eye diseases such as age-related macular degeneration (dry and wet), diabetic retinopathy, vessel occlusions, exudative chorioretinopathy, neovascular glaucoma, retinopathy of prematurity (ROP) or corneal neovascularization. In these cases, intravitreal injections may be the first choice, i. e. injecting a drug or agent (such as Pagaptanib, Ranibizumab, Bevacizumab, Aflibercept, Brolucizumab, steroids or other compounds) directly into the vitreous cavity. Instead or in addition, injections into the anterior region of the eye are also possible. Such injections allow for a highly targeted drug therapy, maximizing therapeutic drug delivery to the treatment site while minimizing systemic toxicity.

The present invention may be used to plan and/or document the injections, including the precise site and dosage information. The corresponding data may be used for planning the further treatment steps.

The inventive method and system may even be used following surgery affecting the appearance of the facial region, including plastic or cosmetic surgery, to monitor the healing process and to detect adverse complications at an early stage.

Preferably, the additional information comprises indications on a desired outcome of the treatment provided by the human subject and/or an attending professional of the human subject. This allows for assessing whether the treatment has the desired effect and whether the treatment may be stopped because its goal has been attained. Indications on a desired outcome are particularly advantageous if the desired outcome is not basically the same in all treatments of the condition (clear skin, remission of blepharitis or a chalazion, complete opening of the eye lid, etc.). This applies in particular to cosmetic treatments.

Preferredly, a preview image representing an expected look of the facial region after treatment according to the obtained treatment recommendation is generated and displayed. This allows in particular for choosing between different treatment regimes or between treatment and non-treatment. Preferably, the preview image is displayed directly to the patient, e. g. on his or her computing device.

The preview image may be a still and/or video image. The effects may be simulated in real-time by augmented reality techniques.

In a preferred embodiment, the modalities of a treatment (e. g. with respect to locations and/or dosage) may be adjusted on a user interface and the expected outcome is displayed essentially in real-time on the same user interface.

The inventive method may include the additional step of a visual acuity test, wherein a result of the visual acuity test forms part of the additional information. Correspondingly, the inventive system comprises a visual acuity test module. Preferably, the visual acuity test is performed with the same software application and the same device as the image acquisition. In particular, a visual acuity test is advisable in connection with a BoNT treatment close to the eye region (which may result in decreased visual acuity in rare cases) or in connection with conditions or treatments that do or may affect the visual faculty of the human subject.

Other advantageous embodiments and combinations of features come out from the detailed description below and the entirety of the claims.

BRIEF DESCRIPTION OF THE DRAWINGS

The drawings used to explain the embodiments show.

In the figures, the same components are given the same reference symbols.

PREFERRED EMBODIMENTS

Figure 1:
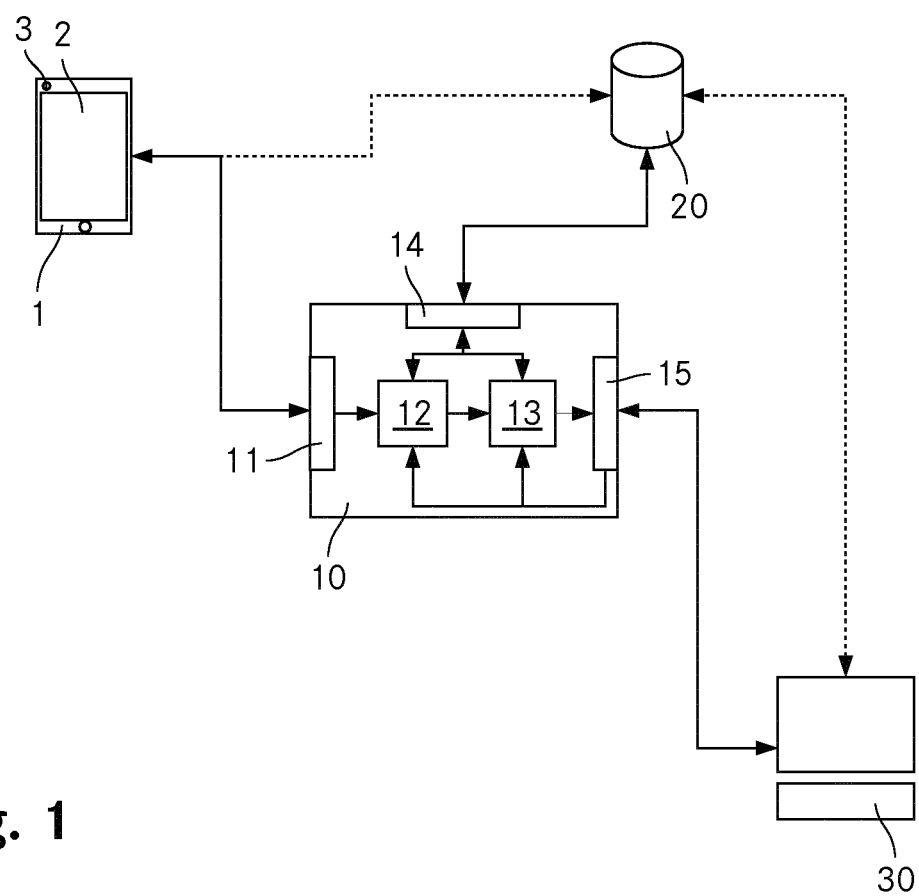
FIG. 1 a block diagram of an embodiment of an inventive system for generating treatment recommendations.

The FIG. 1 is a block diagram of an embodiment of an inventive system for generating treatment recommendations. The system includes a user terminal 1, in the described example this is a smartphone, including inter alia a display 2 and a front camera 3. The user terminal 1 further includes a communication interface for communicating over a mobile network. The front camera 3 is on the same face of the user terminal 1 as the display. This allows for acquiring images of the user, while at the same time displaying information (such as a real-time display of the acquired image or instructions). The display 2 features a touchscreen, such that the user is enabled to operate most of the functions of the user terminal 1 by appropriately touching regions of the touch screen.

The user terminal 1 communicates with a server 10 over the mobile network. For that purpose, the server 10 comprises a mobile network communication interface 11. The server 10 further comprises a processor including a comparison module 12 and a classifying module 13. It is to be noted that in the described example the comparison module 12 and the classifying module 13 are software modules running on the server computer. Data is exchanged between the communication interface 11, the comparison module 12 and the classifying module 13. The server 10 further comprises a second communication module 14 for accessing a cloud storage 20 and a third communication module 15 for communicating with a computer system 30 of an attending professional. Both the second communication module 14 and the third communication module 15 exchange data with the processor of the server 10.

Figure 2A:
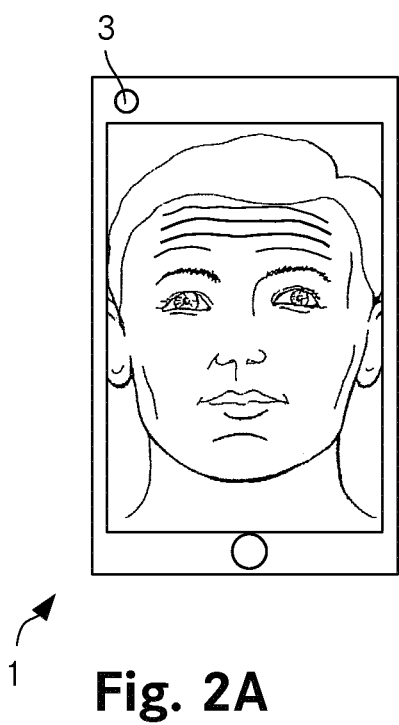
FIG. 2A-G schematic representations of the user interface of the user terminal during several steps of an inventive method for generating treatment recommendations.
Figure 2B:
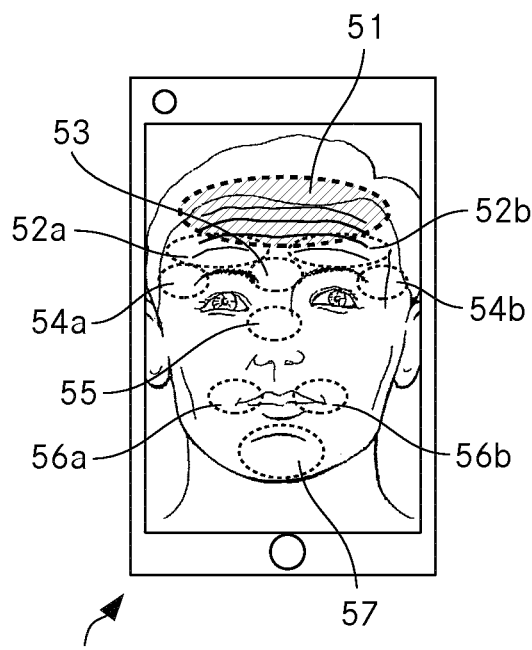
Figure 2C:
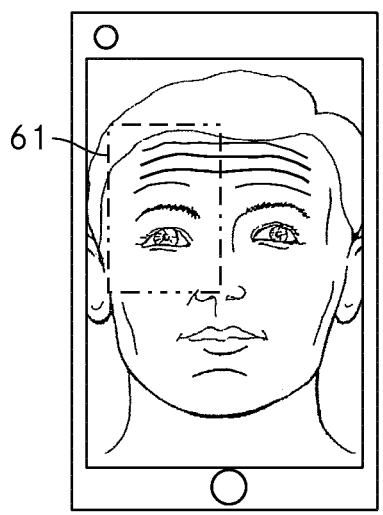
Figure 2D:
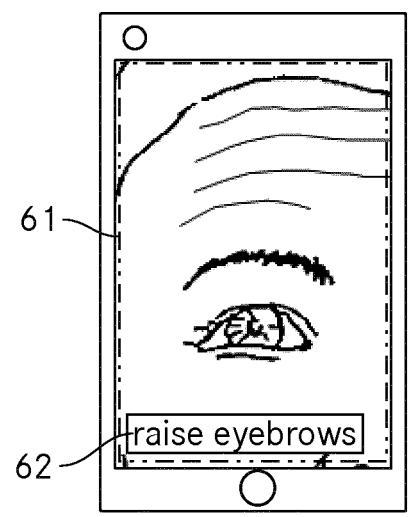
Figure 2E:
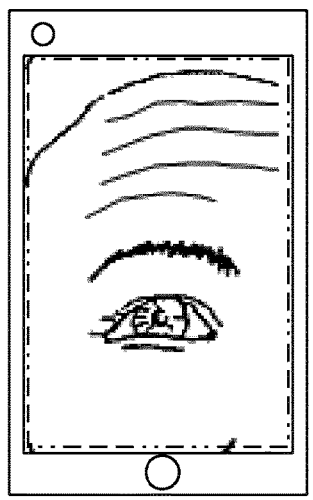

The FIGS. 2A-F are schematic representations of the user interface of the user terminal 1 during several steps of an inventive method for generating treatment recommendations. The described case relates to the treatment of facial wrinkles with BoNT injections. The FIG. 2A is a basic view displaying the image acquired by the front camera 3 basically in real time. The acquired image covers most of the facial region of the user.

In a first step, the treatment areas are defined. For that purpose, possible treatment areas are marked by oval areas overlaid on an acquired still image of the facial area of the user. The correct locations for the areas is determined based on an image recognition process, identifying marked features of the facial region. In the described example, the marked possible treatment areas are the following:

forehead lines (area 51);
eyebrows (areas 52a, 52b);
frown lines (area 53);
crow's feet (areas 54a, 54b);
bunny lines (area 55);
corners of the mouth (areas 56a, 56b); and
chin (area 57).

The user may select areas to be treated by activating the respective area by operating the touchscreen at the respective place(s). In the described example, the user selects the forehead lines area 51. The choice is confirmed by displaying the chosen area(s) by dashing (see FIG. 2B).

In a next step, the user is guided to acquire those images that are needed to assess the present state of the condition to be treated. This may include the taking of detail images of the areas to be treated. For that purpose, a frame 61 denoting the area to be imaged is overlaid the real-time image of the user (see FIG. 2C), and the user repositions the user terminal 1 until the frame roughly corresponds with the display. As soon as this is the case, a still image is automatically acquired (see FIG. 2D).

If the entire facial region relevant for BoNTs treatments shall be covered, usually about 5-8 images will be required (e. g. forehead both sides, lower face just below the eyes to below the chin, right and left side of the face).

In order to enhance relevant structures of the facial region, the user may be asked to assume a certain facial expression. In the described case, the user is asked to raise his eyebrows as high as possible by displaying a corresponding instruction 62 (see FIG. 2D). Both the still image of the user with a relaxed facial expression and of the user with raised eyebrows (FIG. 2E) are stored in the memory of the user terminal 1.

The method may include further substeps for acquiring further images of the relevant facial regions. They may show other facial expressions, other regions of the face or may be taken with different illumination.

The acquired images are sent to the server 10 over the mobile network. In the server 10, the images are processed to generate an initial proposal for a treatment recommendation as described in more detail below. The treatment recommendation is submitted back to the user terminal 1 as well as to the computer system 30 of the attending professional. On the user terminal 1, the proposed treatment recommendations, BoNT injections in the described case, as well as a preview of the look of the facial region after treatment are displayed. The treatment recommendations include the position 63.1 ... 8 and dosage 64.1 ... 8 of several BoNT injections. In the shown example, each dosage 64.1 ... 8 may be individually adjusted by using sliders

Figure 2F:
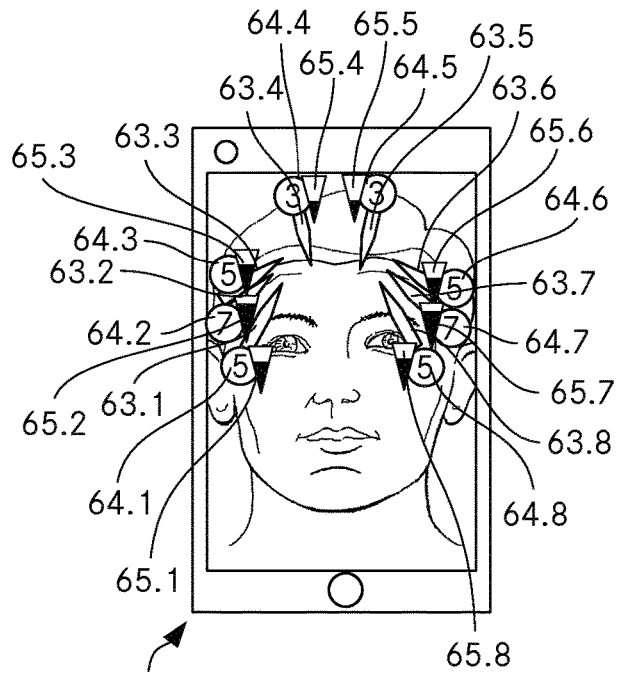
Figure 2G:
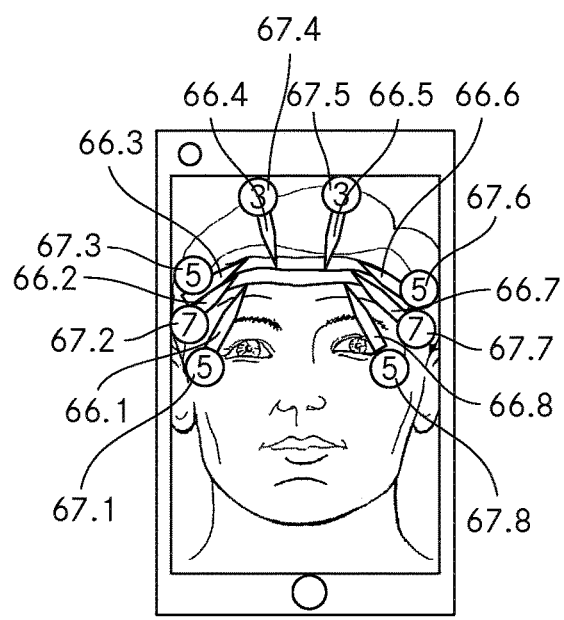

65.1 . . . 8 (see FIG. 2F). The preview is dynamically adjusted, essentially in real-time, such that the user may iteratively adjust the dosages until the previewed result matches with his or her aims. As soon as all adjustments have been made, the choice is accepted. Next, the final treatment recommendation is displayed for information purposes (see FIG. 2G). The treatment recommendations include the position 66.1 . . . 8 and dosage 67.1 . . . 8 of several BoNT injections. The attending professional is provided by the same information; it may be complemented by further information that is relevant for an optimum treatment but that is of little interest for the user.

A visual acuity test may be performed using the user terminal 10 immediately after the capture of the images required for the generation of the treatment recommendation or after presenting the recommendation to the user.

Figure 3A:
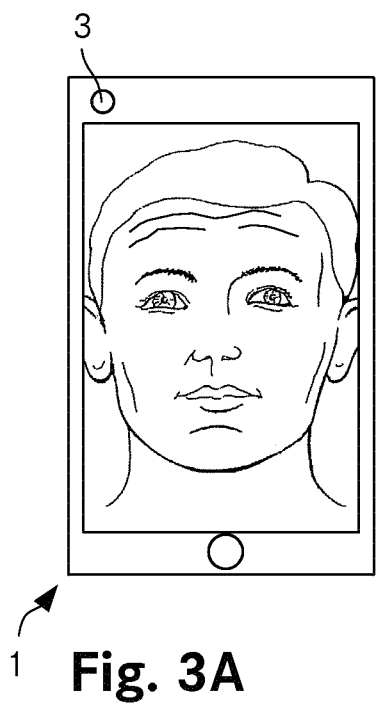
FIG. 3A, B schematic representations of the user interface during a later session of the same user.
Figure 3B:
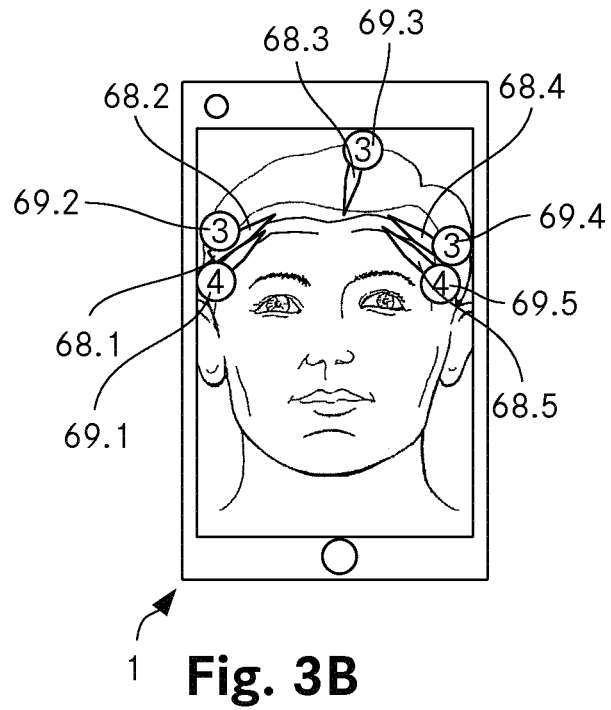

The FIGS. 3A, B are schematic representations of the user interface during a later session of the same user, e. g. some time after treatment of the condition. Again, in the basic view the image acquired by the front camera 3 is displayed basically in real time. As can be seen from FIG. 3A, the forehead lines have lessened. Essentially, the same method for obtaining a treatment recommendation is repeated. The FIG. 3B shows the resulting treatment recommendation. Instead of eight proposed injections the number is reduced to five (positions 68.1 . . . 5) and the dosage 69.1 . . . 5 is reduced.

Figure 4:
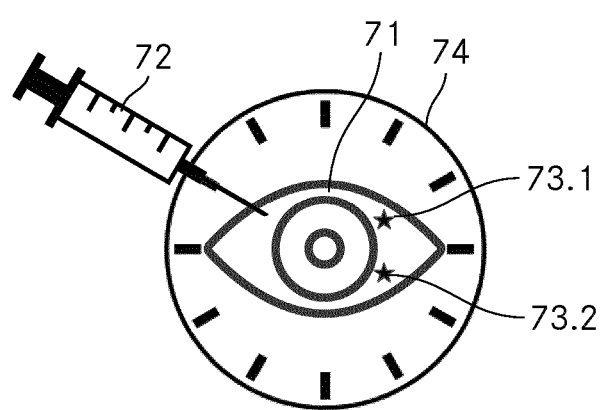
FIG. 4 an example of an indicative display for eye treatments.

The FIG. 4 is an example of an indicative display for eye treatments. It comprises the image 71 of the eye to be treated by an intravitreal injection or any other eye site injection. A syringe symbol 72 is superimposed to indicate the proposed injection site (tip of the syringe). Previous injections (during the same session or earlier sessions) are indicated by star symbols 73.1, 73.2. Finally, a clock face symbol 74 is superimposed to help the user finding the appropriate site. In the shown example, an injection at 10 o'clock is suggested, in a site slightly outside the eye's iris region. Again, in addition, a dosage recommendation may be displayed (not shown in FIG. 4).

In the described example, the processing of the image data on the server 10 includes the following steps:

In a first step, the image data is preprocessed to improve the suitability of the image for the subsequent processing steps. This includes processing steps that are known as such, such as noise reduction, contrast enhancements, colour normalization, etc. Usually, the application on the user terminal 1 will control the front camera 3 of the user terminal 1 as well as the processing of the images on the user terminal 1 in such a way that the amount of filtering and corrections on the user terminal 1 is minimized. As an example, it would be counterproductive if the images taken by the front camera 3 are automatically subject to a smoothing step as this would hinder the detection of e. g. wrinkles or skin irritations. Nevertheless, in principle preprocessing steps such as filtering steps on the user terminal 1 may be used if their effect is known and if they do not reduce the relevant information content of the image data. This allows for simplifying the preprocessing step on the server.

The preprocessing may include the steps of consolidating a plurality of pictures into one, e. g. in order to improve the image quality or to supplement the covered area of the facial region.

Optionally, a plurality of 2d images (from different viewing angles and/or taken using different illumination) may be processed to obtain a 3d model of the facial region, using methods known as such.

After preprocessing, the image data will be processed by an image recognition process to detect prominent features of the facial region that are represented by the image data (such as eyes, eyebrows, mouth, nostrils, bridge of the nose, etc.). This allows for comparing the image data with previously taken images and/or with reference data relating to specific areas of the facial region. A detailed mesh may be defined, based on the detected features (landmarks), c. f. e. g. J. Clement, M. Marks: "Computer-Graphic Facial Reconstruction", Academic Press, 2005. Based on the results of the image recognition process, a certain section of the image is designated for the further analysis.

The corresponding image data is fed to a machine learning process for classifying the image with respect to the treatment recommendation to be obtained, taking into account additional information provided, including indications about a desired outcome (or a default indication, if no user-specific information is available). In particular, a multi-label classification method is employed that allows for providing multi-dimensional treatment recommendations. In the given example, only the subregions of the facial region chosen by the user will be processed, i. e. the forehead lines area 51. The machine learning process has access to input information relating to a considerable number of BoNT treatments of this area, including information on the visual appearance before and after the treatment as well as on the treatment itself, including in particular injection positions and dosage. All information is anonymized and pooled and delivered to the server in a HIPAA compliant encrypted way. The datasets may be complemented by further information, e. g. on the patient (gender, age, skin type, etc.) or on the treatment (follow-up treatment steps, treatment interval, specific composition used, etc.). All this information may be taken into account in the machine learning process. The process may include the generation of heatmaps representing the change over time (e. g. before/after a certain kind of treatment or the actual treatment provided to the user in the past).

The machine learning process may be complemented by an optimization step, in particular if several areas are treated and/or if several kinds of treatment are combined. The overall expected result of the treatment, represented by a score, may be optimized based on a numerical optimization process.

Both the optimization as well as the machine learning process may be based on scales (metrics) that have been developed, e. g. scales measuring the degree of ageing and the severity of facial wrinkles in the field of non-surgical cosmetic procedures. The scales provide an objectified framework for evaluating the level of improvement resulting from cosmetic procedures.

Suitable techniques for both image recognition and machine learning based on images of the facial region are known from other fields, c. f. e. g. Y. Taigman et al.: "DeepFace: Closing the Gap to Human-Level Performance in Face Verification", Proceedings of 2014 IEEE Conference on Computer Vision and Pattern Recognition; M. Y. Hajeer et al.: "Three-dimensional imaging in orthognathic surgery: The clinical application of a new method", Int J Adult Orthod Orthognath Surg, Vol. 17, No. 4, 2002; R. A. Al-Sanea et al.: "3D Facial Soft Tissue Changes Due to Orthodontic Tooth Movement", InTech, 2012.

Finally, the obtained treatment recommendation is forwarded to the user terminal 1 and the computer system 30 of the attending professional and suitably displayed (wherein different kinds of displaying may be used for the user and the attending professional).

The image data, treatment recommendations and further data obtained from the user, from the attending professional or a third party will be securely stored in the cloud storage 20 and may be accessed during a personal meeting of the user with his or her attending professional or remotely from the user terminal 1 or the computer system 30. Automatic data exchange with standard EMR (electronic medical record) messaging is available.

Images may also be obtained by the computer system 30 of the attending professional. Accordingly, data obtained during a personal visit may be processed just as data obtained remotely, using the user terminal 1. Basically, examinations shall be repeated remotely and/or in person in regular intervals. All obtained data will be stored in the cloud storage 20, supplemented by a time stamp. Unauthorized access is prohibited using appropriate security measures. This allows for monitoring the course and the effects of the treatments and for adjusting the further treatment based on the experience so far and the expectations of the user.

The invention is not restricted to the described embodiment. In particular, it may be used in connection with other conditions, and the detailed aspects of the method and system may be embodied differently.

In summary, it is to be noted that the invention creates a method and a device for generating treatment recommendations that allows for an improvement of the treatment of conditions that affect the appearance of a facial region of a human subject.

We claim:

1. A method for generating treatment recommendations based on images of a facial region of a human subject, comprising the steps of:
   a) acquiring at least one image of the facial region using a camera and generating image data representing the at least one image;
   b) processing the image data and additional information with a processor to obtain a treatment recommendation, wherein the additional information includes at least an indication of a condition affecting an appearance of the facial region and an indication of a treatment type to treat the condition, wherein the treatment type is one of local injections of a substance, external application of a substance, intake of a composition, internal use of a certain pharmaceutical substance, or combinations thereof;
   c) outputting the obtained treatment recommendation to a display screen or to a further computer;
   wherein the step of processing the image data includes improving the image quality, identifying and/or measuring facial structures and/or generating statistical data,
   wherein the processing step includes a comparison substep to compare with a comparison module of the processor information derived from the image data with reference information to obtain a reference measure, the reference measure being an assessment of the severity of a condition, an assessment of the effects of the condition on appearance compared to a standard, a target state or a comparison individual or group and/or an assessment of progression or regression of the condition compared to an earlier point in time, wherein the reference measure is selected from a group consisting of a binary information, a ternary information, a value, and a multi-dimensional quantity, and
   wherein the processing step further includes a classifying substep which is based on the reference measure and yields the treatment recommendation, wherein the treatment recommendation includes at least one of the following:
   a treatment substance recommendation;
   a dosage recommendation;
   a treatment location recommendation;
   a treatment timing recommendation;
   an examination recommendation.

2. The method as recited in claim 1, wherein the comparison substep and the classifying substep include the application of a machine learning algorithm.

3. The method as recited in claim 1, wherein the image is acquired by a computing device of the human subject, that the image data is transmitted from the mobile computing device to a server and that the processing step is carried out by the server based on the received image data.

4. The method as recited in claim 1, wherein the acquiring step includes acquiring a plurality of images of the facial region.

5. The method as recited in claim 4, wherein the acquiring step includes acquiring video images of the facial region.

6. The method as recited in claim 1, wherein the reference information comprises image data obtained from an image of the facial region of the human subject taken at an earlier point in time.

7. The method as recited in claim 1, wherein the acquiring step includes a substep of providing instructions to the human subject affecting the at least one acquired image of the facial region.

8. The method as recited in claim 7, wherein the substep of providing instructions includes an instruction to the human subject to assume a certain facial expression.

9. The method as recited in claim 1, wherein the condition is an aesthetic condition and in that the treatment type is a cosmetic treatment.

10. The method as recited in claim 9, wherein the cosmetic treatment comprises an application of botulinum neurotoxin injections in the facial region.

11. The method as recited in claim 9, wherein the cosmetic treatment comprises an application of gel filler injections in the facial region.

12. The method as recited in claim 9, wherein the additional information comprises indications on a desired outcome of the treatment provided by the human subject and/or an attending professional of the human subject.

13. The method as recited in claim 1, wherein a preview image representing an expected look of the facial region after treatment according to the obtained treatment recommendation is generated and displayed.

14. The method as recited in claim 1, comprising the additional step of a visual acuity test, wherein a result of the visual acuity test forms part of the additional information.

15. The method as recited in claim 1, wherein it is possible to provide a number of treatment types in order to provide recommendations including more than one treatment type if suitable.

16. A system for generating treatment recommendations based on images of a facial region of a human subject, comprising
   a) a camera for acquiring at least one image of the facial region and generating image data representing the at least one image;
   b) a processor for processing the image data and additional information to obtain a treatment recommendation, wherein the additional information includes at least an indication of a condition affecting an appearance of the facial region and an indication of a treatment type to treat the condition, wherein the treatment type is one of local injections of a substance, external application of a substance, intake of a composition, internal use of a certain pharmaceutical substance, or combinations thereof;

c) an interface for outputting the obtained treatment recommendation to a display screen or to a further computer;

wherein the step of processing the image data includes improving the image quality, identifying and/or measuring facial structures and/or generating statistical data, wherein the processor includes a comparison module to compare information derived from the image data with reference information to obtain a reference measure, the reference measure being an assessment of the severity of a condition, an assessment of the effects of the condition on appearance compared to a standard, a target state or a comparison individual or group and/or an assessment of progression or regression of the condition compared to an earlier point in time, wherein the reference measure is selected from a group consisting of a binary information, a ternary information, a value, and a multi-dimensional quantity, and wherein the processor further includes a classifying module to obtain the treatment recommendation based on the reference measure, wherein the treatment recommendation includes at least one of the following:
- a treatment substance recommendation;
- a dosage recommendation;
- a treatment location recommendation;
- a treatment timing recommendation;
- an examination recommendation.

17. The system as recited in claim 16, further comprising an acquisition module for guiding the human subject to acquire the at least one image.

18. The system as recited in claim 17, wherein the camera is comprised by a computing device of the human subject, the computing device further comprising the acquisition module and a first transmitter module to transmit image data, and that the processor is comprised by a server including a second transmitter module for receiving the image data from the computing device.

19. The system as recited in claim 16, wherein it is possible to provide a number of treatment types in order to provide recommendations including more than one treatment type if suitable.

20. A method for generating treatment recommendations based on images of a facial region of a human subject, comprising the steps of:

a) acquiring at least one image of the facial region using a camera and generating image data representing the at least one image;

b) processing the image data and additional information with a processor to obtain a treatment recommendation, wherein the additional information includes at least an indication of a condition affecting an appearance of the facial region and an indication of a treatment type to treat the condition, wherein the treatment type is one of local injections of a substance, external application of a substance, intake of a composition, internal use of a certain pharmaceutical substance, or combinations thereof;

c) outputting the obtained treatment recommendation to a display screen or to a further computer;

wherein the step of processing the image data includes improving the image quality, identifying and/or measuring facial structures and/or generating statistical data, wherein the processing step includes a comparison substep to compare with a comparison module of the processor information derived from the image data with reference information to obtain a reference measure, the reference measure being an assessment of the severity of a condition, an assessment of the effects of the condition on appearance compared to a standard, a target state or a comparison individual or group and/or an assessment of progression or regression of the condition compared to an earlier point in time, wherein the reference measure is selected from a group consisting of a binary information, a ternary information, a value, and a multi-dimensional quantity, and wherein the processing step further includes a classifying substep which is based on the reference measure and yields the treatment recommendation, wherein the treatment recommendation includes at least one of the following:
- a treatment substance recommendation;
- a dosage recommendation;
- a treatment location recommendation;
- a treatment timing recommendation;
- an examination recommendation wherein all steps of the method are executed by a computer program product comprising program code run on a computer system.

21. The method as recited in claim 20, wherein it is possible to provide a number of treatment types in order to provide recommendations including more than one treatment type if suitable.

* * * * *